(12) United States Patent
Gagel et al.

(10) Patent No.: US 9,320,843 B2
(45) Date of Patent: Apr. 26, 2016

(54) DEVICE AND METHOD FOR MONITORING AN EXTRACORPOREAL BLOOD CIRCUIT FOR THE DETECTION OF AIR BUBBLES

(71) Applicant: Fresenius Medical Care Deutschland GmbH, Bad Homburg v.d.H (DE)

(72) Inventors: Alfred Gagel, Litzendorf (DE); Gerhard Wiesen, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 316 days.

(21) Appl. No.: 14/102,893

(22) Filed: Dec. 11, 2013

(65) Prior Publication Data

US 2014/0166579 A1   Jun. 19, 2014

Related U.S. Application Data

(60) Provisional application No. 61/736,672, filed on Dec. 13, 2012.

(30) Foreign Application Priority Data

Dec. 13, 2012   (DE) .......................... 10 2012 024 341

(51) Int. Cl.
*B01D 35/00*   (2006.01)
*A61M 1/36*   (2006.01)

(52) U.S. Cl.
CPC ..... *A61M 1/3626* (2013.01); *A61M 2205/3331* (2013.01); *A61M 2205/3351* (2013.01); *A61M 2230/207* (2013.01)

(58) Field of Classification Search
CPC .................. A61M 1/3626; A61M 2205/3331; A61M 2205/3351; A61M 2230/207

USPC ...................... 210/647, 85, 90; 435/287.1, 29
See application file for complete search history.

(56) References Cited

U.S. PATENT DOCUMENTS

2002/0134134 A1   9/2002   Derek et al.
2003/0009123 A1*  1/2003   Brugger .............. A61M 1/3626
                                                            604/4.01

(Continued)

FOREIGN PATENT DOCUMENTS

EP   1260238 A2   11/2002

OTHER PUBLICATIONS

International Preliminary Report on Patentability dated Jun. 16, 2015 in PCT/EP2013/003478.

(Continued)

*Primary Examiner* — Dirk Bass
(74) *Attorney, Agent, or Firm* — Kenyon & Kenyon LLP

(57) ABSTRACT

A device for monitoring an extracorporeal blood circuit of an extracorporeal blood treatment device for detection of air bubbles in blood that is conveyed in the extracorporeal circuit by a blood pump, and a method for monitoring an extracorporeal blood circuit for detection of air bubbles, together with a device for monitoring the extracorporeal blood circuit are described. The device and method are based on monitoring the negative pressure in the extracorporeal blood circuit upstream of the blood pump, to allow differentiation between the occurrence of microbubbles which are attributable to cavitation and an entry of air not due to cavitation. When the negative pressure is above a predetermined limit value and microbubbles are detected in the extracorporeal blood circuit, it is deduced that the microbubbles are produced by cavitation and the mechanisms for dissolving the microbubbles are insufficient to remove the microbubbles again before they could reach the patient.

17 Claims, 1 Drawing Sheet

(56) References Cited

U.S. PATENT DOCUMENTS

| | | |
|---|---|---|
| 2007/0062861 A1 | 3/2007 | Lannoy |
| 2008/0171960 A1 | 7/2008 | Brieske et al. |
| 2010/0130905 A1* | 5/2010 | Nurnberger ......... A61M 1/3672 604/6.07 |
| 2010/0274172 A1 | 10/2010 | Guenther et al. |

OTHER PUBLICATIONS

Interventionelle Kardiologie, Angiologie and Kardiovaskularchirugie, Stuttgart: Schattauer, 2001, pp. 229, 239 (ISBN 3-7945-1931-0) [English Abstract attached].

* cited by examiner

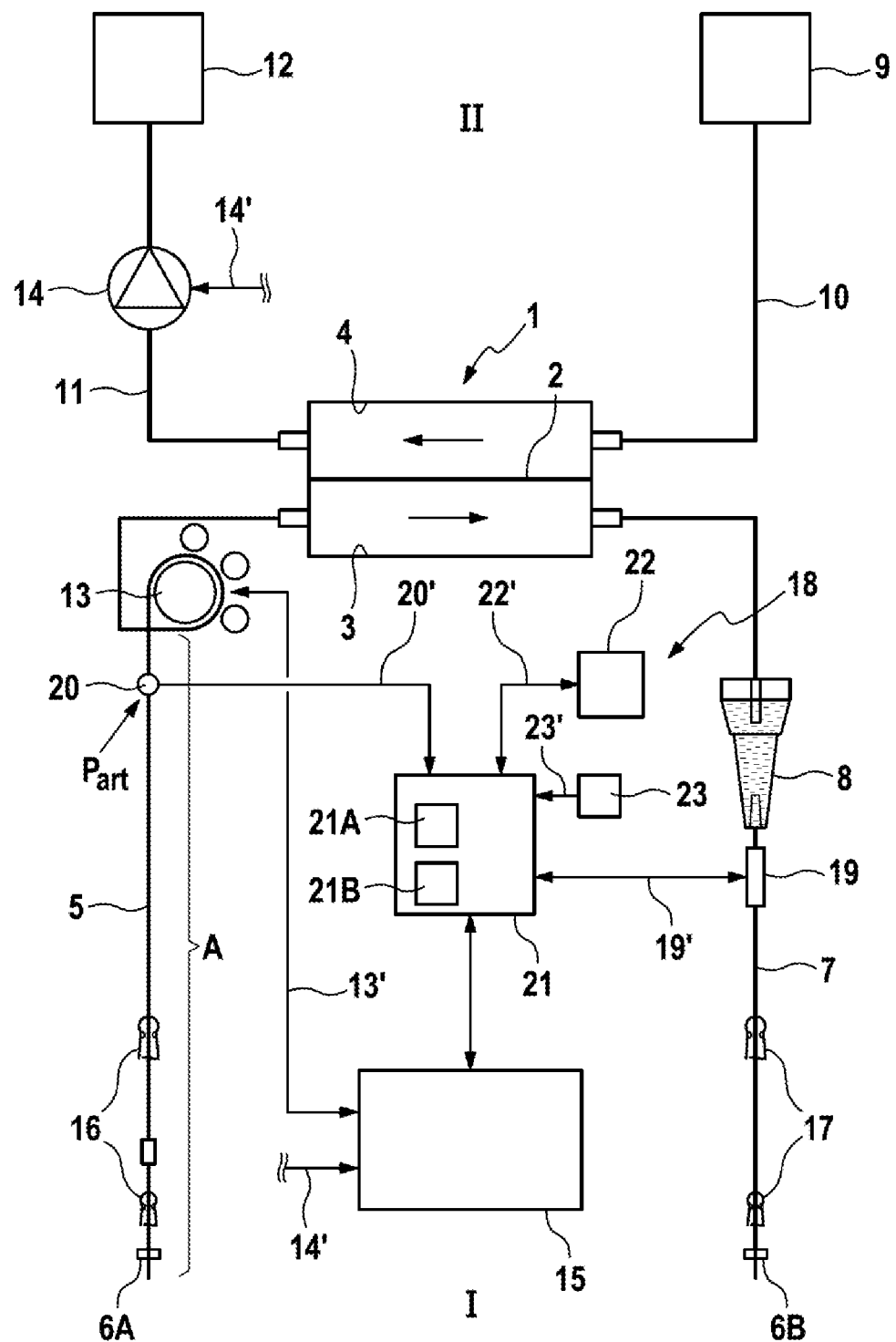

DEVICE AND METHOD FOR MONITORING AN EXTRACORPOREAL BLOOD CIRCUIT FOR THE DETECTION OF AIR BUBBLES

CROSS REFERENCE TO RELATED APPLICATION

The present application claims priority to Application No. DE 10 2012 024 341.3, filed in the Federal Republic of Germany on Dec. 13, 2012, and U.S. Provisional Patent Application Ser. No. 61/736,672, filed on Dec. 13, 2012, each of which is expressly incorporated herein in its entirety by reference thereto.

FIELD OF INVENTION

The present invention relates to a device for monitoring an extracorporeal blood circuit of an extracorporeal blood treatment device to detect air bubbles in the blood, which is conveyed in the extracorporeal circuit by a blood pump. The present invention further relates to a method for monitoring an extracorporeal blood circuit to detect air bubbles as well as a device for extracorporeal blood treatment with a device for monitoring the extracorporeal blood circuit.

BACKGROUND INFORMATION

Various methods are known for extracorporeal blood treatment, in which the blood of the patient flows in an extracorporeal blood circuit through a blood treatment unit. The possibility of penetration of air into the extracorporeal blood circuit represents one of the fundamental complications of extracorporeal blood treatment, for example, haemodialysis or haemofiltration.

The known drip chambers, which are positioned in the venous branch of the extracorporeal blood circuit downstream of the blood treatment unit, are used for separation of entrained air bubbles from the blood. The known drip chambers intercept the air bubbles with a high degree of certainty. Nevertheless, there is basically the risk that air bubbles are infused into the patient intravenously. Therefore, for further increase of safety, apparatuses are provided in blood treatment devices with which the occurrence of air bubbles can be detected.

Apparatuses for detection of air bubbles and blood are described, for example, in German Application Nos. DE 102 09 254, DE 10 2005 025 500 and DE 2005 025 515. The known air detectors are based on the difference of absorption of ultrasound in liquid and gaseous media as well as the scattering of ultrasound at interfaces. For detection of air, signal pulses are coupled into the blood, while the signal pulses exiting from the blood are received. It can be concluded from this that air is present when the received signal falls below a reference value. Apart from ultrasonic sensors, air detectors are also known that are based on the different dielectric constants and conductivities of liquid and gaseous media.

The formation of smaller or larger air bubbles in blood can have different causes. Possible causes for the penetration of air are a leak in the tube line system, a fall in the blood level in the venous drip chamber or a single entry of air during an infusion of a drug into the extracorporeal blood circuit. However, microbubbles, which derive from cavitation, can also occur in the blood.

In general, occluding blood pumps are used for conveying blood, in particular roller pumps, which have several rollers with which the tube line is occluded, as a result of which a pulsating blood flow is produced. On the input side, the pump produces a negative pressure in the blood line and, on the outlet side, a positive pressure. The negative pressure on the suction side of the pump is due to a constriction of the flow cross-section in the cannula for connection to the patient, while the outlet side positive pressure is determined by the resistance to flow in the tube line system.

In the tube line upstream of the blood pump, cavitation can lead to the formation of microbubbles. The number of microbubbles typically increases from the arterial cannula to the arterial blood line and to the outlet of the blood pump. The marked increase at the outlet of the pump can be explained by the especially strong cavitation as the roller of the roller pump lifts, with a brief minimum clearance between roller and tube, and a high pressure gradient between pump inlet and outlet. The microbubbles, once created, are exposed to a positive pressure, downstream of the pump in the tube line system, due to which they can continually be dissolved again. Furthermore, in the blood treatment unit, in particular in the dialysis machine, the number of microbubbles is reduced by exchange for degassed dialysis fluid, as a result of dissolved air from the bloodstream passing via the dialysis machine into the degassed dialysate. Thus, the re-solubility of the blood increases, because of which the number of microbubbles in the blood sharply decreases.

A certain number of cavitation-related microbubbles can be re-dissolved in the tube line system and the dialysis machine insofar as they are no longer detected by the devices with which the number of air bubbles occurring in a predetermined time interval is compared with a threshold value. However, intensified cavitation leads to a larger number of air bubbles, which is detected by the monitoring devices. If a specific threshold value is exceeded during the treatment, the monitoring device triggers an alarm. Since large quantities of microbubbles are in the tube section between the venous drip chamber and the venous cannula at the time when the threshold value is exceeded, the blood treatment must be stopped for separation of the microbubbles. After dialysis has been stopped, the patient must be separated from the arterial and venous blood line and the ends of the tubes have to be short-circuited with a special adapter, in order to pump the blood to the extracorporeal blood circuit. While the blood slowly recirculates in the closed circuit, the microbubbles can be dissolved or can be separated in the venous drip chamber. The patient must then be re-connected to the extracorporeal blood circuit.

By monitoring the extracorporeal blood circuit, the occurrence of microbubbles is detected, an alarm is triggered, and the medical personnel are prompted to initiate the necessary measures to eliminate the infusion of microbubbles. However, there is a disadvantage that interruption of treatment is connected with increased effort for the medical personnel and inconvenience for the patient.

The measures to be initiated when cavitation-related air bubbles appear are different from the measures that are necessary when microbubbles occur due to micro-leaks in the tube line system or the lowering of the blood level in the drip chamber.

SUMMARY

Therefore an object of the present invention is to provide a device for monitoring an extracorporeal blood circuit that allows differentiation between a cavitation-related formation of microbubbles and a non-cavitation-related entry of air.

A further object of the present invention is to provide a method for monitoring an extracorporeal blood circuit that allows differentiation between a cavitation-related and a non-cavitation-related formation of microbubbles.

An object of the present invention is also to provide a device for extracorporeal blood treatment with such a device for monitoring an extracorporeal blood circuit.

The device in accordance with the present invention and the method in accordance with the present invention are based on monitoring the negative pressure in the extracorporeal blood circuit upstream of the blood pump, to allow differentiation between the formation of microbubbles that can be attributed to cavitation and entry of air, which is not caused by cavitation.

Tests have shown that cavitation-related formation of air bubbles upstream of the blood pump can occur when the value of the negative pressure in the section of the tube line of the extracorporeal blood circuit upstream of the pump exceeds a specific limit value. The assumption here is that microbubbles are not produced by cavitation below this threshold value. The critical level for the average negative pressure can be 180-190 mmHg, for example.

The monitoring apparatus in accordance with the present invention comprises an apparatus for measuring the negative pressure in the extracorporeal blood circuit and a processing unit, which is configured so that a first defective condition is deduced when the device for detecting the occurrence of air bubbles in the extracorporeal blood circuit detects air bubbles and the measured negative pressure is above the predetermined limit value for the negative pressure and/or a second defective condition is deduced when the device for detecting the occurrence of air bubbles in the extracorporeal blood circuit detects air bubbles and the measured negative pressure is less than the predetermined limit value for the negative pressure. It is therefore assumed that the first defective condition, which differs from the second defective condition, is the cavitation-related formation of microbubbles. In this connection, negative pressure is understood to be the magnitude of the negative pressure, i.e., the limit value for the negative pressure is exceeded when the measured negative pressure is above the critical threshold.

When the negative pressure is above the predetermined limit value and microbubbles are detected in the extracorporeal blood circuit, it is concluded that microbubbles are produced by cavitation and the mechanisms for dissolving the microbubbles are not sufficient to remove the microbubbles again before they could reach the patient.

The device in accordance with the present invention and the method in accordance with the present invention provide for the risk of a formation of microbubbles to be indicated at a time at which the number of microbubbles measured in a time interval is generally still below the threshold value above which interruption of blood treatment is prompted. Consequently, the medical personnel can react at an early stage to the risk of the formation of microbubbles with the necessary measures. For example, the medical personnel can reduce the blood flow rate, which leads to a reduction of the negative pressure and thus of microbubble formation. In the next dialysis treatment, a cannula with a larger cross-section can be used, enabling higher blood flows at lower negative pressures.

In the case where the measured negative pressure is below the predetermined limit value, it is concluded that cavitation-related microbubble formation does not exist. In this case, for example, micro-leaks in the arterial tube line system upstream of the blood pump, including the heparin or infusion lines, can be the cause for microbubble formation. A further cause in this case can be the fall of the blood level in the venous drip chamber, so that the blood is not introduced under the blood level at the regularly set level, at which the entrainment of air at the blood/air boundary is avoided. However, if the blood inlet is at the level of the blood level or even higher, air in the form of microbubbles is introduced by the blood flowing into the blood volume of the drip chamber. This effect can occur before the drop in the blood level in the drip chamber is detected. Thus detection of a non-cavitation-related microbubble formation can not only prompt checking of the tube line system but also of the level setting required in the drip chamber.

A preferred exemplary embodiment of the present invention provides that the number of air bubbles occurring in a predetermined time interval is determined, wherein the processing unit is configured so that a first defective condition is deduced when the measured negative pressure is above the predetermined limit value for the negative pressure and the number of air bubbles in the predetermined time interval is greater than the predetermined limit value for the rate of air bubbles and/or a second defective condition is deduced when the measured negative pressure is less than the predetermined limit value for the negative pressure and the number of air bubbles in the predetermined time interval is greater than the predetermined limit value for the rate of air bubbles. In this exemplary embodiment, it is thus not sufficient for the detection of a defective condition that the occurrence of microbubbles is detected but that a specific microbubble rate is exceeded, wherein a differentiation is made once more between a cavitation-related and a non-cavitation-related formation of microbubbles.

In tests, it has further been shown that the limit value for the negative pressure, below which a cavitation-related microbubble formation is assumed, is dependent on the patient. It has been shown that the limit value depends in particular on the haematocrit of the blood.

In a particularly preferred exemplary embodiment, the processing unit is configured so that the limit value for the negative pressure is specified as a function of the haematocrit. In this, the limit value for the negative pressure reduces as the level of the haematocrit increases. For example, different limit values for different values of haematocrit can be stored in a memory, which can be read by the processing unit. However, the limit value can also be calculated using a predetermined mathematical relationship. The haematocrit can in turn be specified or can be measured. An apparatus can be provided for measuring the haematocrit, producing a measurement signal correlated with the haematocrit that the processing unit receives.

When the first and/or second defective condition is deduced, the processing unit preferably generates a control signal. The processing unit can generate different control signals for the two defective conditions, in order to allow differentiation of the two conditions.

In a further exemplary embodiment, an alarm unit is provided, receiving the control signal from the processing unit, and giving an acoustic, optical and/or tactile alarm when the alarm unit receives a control signal from the processing unit.

The blood flow rate can be decreased by the doctor, to reduce the risk of microbubble formation. In principle, an automatic intervention in the blood treatment is possible when the control unit of the blood treatment device is configured so that the blood flow rate is reduced from a predetermined first rate to a predetermined second rate, when the apparatus for detection of the occurrence of bubbles in the extracorporeal blood circuit detects air bubbles and the measured negative pressure is above the specified limit value for the negative pressure.

An exemplary embodiment of the present invention is explained in detail in the following with reference to the accompanying drawing.

BRIEF DESCRIPTION OF THE DRAWING

The FIGURE shows, in a simplified schematic representation, components of a blood treatment device, which has the monitoring device in accordance with the present invention.

DETAILED DESCRIPTION

The blood treatment device, for example, a haemodialysis device, comprises a dialysis machine 1, which is separated by a semipermeable membrane 2 into a blood chamber 3 and a dialysis fluid chamber 4. The inlet of the blood chamber is connected to one end of an arterial blood supply line 5, while the outlet of the blood chamber 3 is connected to a venous blood discharge line 7, which incorporates a venous drip chamber 8. The other ends of the blood supply and discharge lines 5, 7 are connected to an arterial or venous cannula 6A, 6B. Arterial and venous tube clamps 16, 17 are provided on the tube lines. The blood supply and discharge lines 5, 7, together with the blood chamber 3 of the dialysis machine 1, represent the extracorporeal blood circuit I of the haemodialysis apparatus.

The dialysis fluid system II of the dialysis apparatus comprises a dialysis fluid source 9, from which a dialysis fluid supply line 10 leads to the dialysis fluid chamber 4 of the dialysis machine 1. A dialysis fluid discharge line 11 leads from the dialysis fluid chamber 4 to an outlet 12.

An occluding blood pump 13, in particular roller pump, is positioned in the blood supply line 5, while a dialysis fluid pump 14 is positioned in the dialysis fluid discharge line 11. During the blood treatment, blood pump 13 and dialysis fluid pump 14 convey blood in the extracorporeal blood circuit I and dialysis fluid in the dialysis fluid system II.

The haemodialysis apparatus further comprises a central control unit 15, which is connected by control lines 13', 14' to the blood pump 13 or dialysis fluid pump 14. The control unit 15 specifies a blood or dialysis fluid flow rate for the blood and dialysis fluid pumps.

The haemodialysis apparatus further comprises a device 18 for monitoring the extracorporeal blood circuit I which is part of the haemodialysis apparatus in the present exemplary embodiment, but also can form a separate subassembly.

The monitoring device 18 comprises an apparatus 19 for detecting the occurrence of microbubbles which, as such, is part of the state of the art. Apparatuses of this type are described, for example, in German Application Nos. DE 10 2005 025 515 or DE 10 2005 025 500. This apparatus 19, which comprises an ultrasonic transmitter and an ultrasonic receiver, which are located downstream of the drip chamber 8 on the venous blood line 7, determines the microbubbles occurring in a predetermined time interval downstream of the drip chamber, i.e., the microbubble rate. The monitoring apparatus 18 further comprises an apparatus 20 for measuring the negative pressure $P_{art}$ in the portion A of the arterial tube line 5 upstream of the blood pump 13. Both apparatuses 19, 20, are connected by means of data lines 19', 20' to a processing unit 21 of the monitoring device 18. With the exception of the sensors, i.e., the ultrasonic transmitter and receiver, as well as the pressure sensor, all components of the monitoring device can be part of the central processing unit (microprocessor), which in turn can be part of the central control unit 15 of the blood treatment apparatus, wherein a program (software) runs on the control unit, according to which the individual process steps are executed. An alarm unit 22 is connected by means of a further data line 22' and gives an acoustic, optical and/or tactile alarm when it receives an alarm signal from the processing unit 21.

The processing unit 21 comprises a first and a second comparator 21A, 21B. The first comparator 21A compares the number of microbubbles determined in a specified time interval with the predetermined first limit value for the microbubble rate, while the second comparator 21B compares the value of the measured negative pressure $P_{art}$ in the arterial tube line portion A upstream of the blood pump 13 with a predetermined second limit value, which represents a critical threshold for the occurrence of cavitation-related microbubbles. The second limit value is, for example, 180-190 mmHg. When the microbubble rate is above the first limit value and the value of the negative pressure is above the second limit value, the processing unit 21 generates a control signal and a first alarm signal. The alarm unit then gives a first alarm, which signals that cavitation-related microbubble formation exists. As a result, the necessary countermeasures can be initiated. For example, the blood flow rate can be reduced. In the present exemplary embodiment, the control unit 21 can also provide an automatic reduction of blood flow rate from a value previously set for the blood treatment to a lower value when the control unit receives the control signal from the processing unit.

The processing unit 21 generates a second alarm signal when the microbubble rate is above the first limit value and the value of the negative pressure is under the second limit value. Then, there is no formation of cavitation-related microbubbles, so that other countermeasures can be taken.

It has been shown in tests that the degassing phenomenon, which might only occur with a relatively large negative pressure, also depends on the haematocrit of the blood. At the same arterial negative pressure, higher microbubble rates have been measured at high haematocrit, while at low haematocrit smaller microbubble rates were measured. The monitoring apparatus 18 can also comprise an apparatus 23 for measuring the haematocrit, which is also shown only in outline. This apparatus 23 generates a measurement signal correlated with the haematocrit, which is received by the processing unit 21 via a data line 23', wherein the processing unit is configured so that it specifies the second limit value as a function of the measurement signal. When doing this, the processing unit specifies a lower limit value at a high haematocrit and a higher limit value at a lower haematocrit.

What is claimed is:

1. A device for monitoring an extracorporeal blood circuit in which a blood pump is disposed to convey blood, comprising:
    an apparatus adapted to detect an occurrence of air bubbles in blood that flows in the extracorporeal blood circuit,
    an apparatus adapted to measure a negative pressure in the extracorporeal blood circuit upstream of the blood pump, and
    a processing unit programmed to deduce a first defective condition when the apparatus adapted to detect the occurrence of air bubbles in the extracorporeal blood circuit detects air bubbles and the measured negative pressure is above a predetermined limit value for the negative pressure, and/or a second defective condition when the apparatus adapted to detect the occurrence of air bubbles in the extracorporeal blood circuit detects air bubbles and the measured negative pressure is below the predetermined limit value for the negative pressure,
    wherein the first defective condition differs from the second defective condition.

2. The device according to claim 1, wherein the apparatus adapted to detect the occurrence of air bubbles is adapted to determine a number of air bubbles occurring in a predetermined time interval,
wherein the processing unit is programmed to deduce the first defective condition when the measured negative pressure is above the predetermined limit value for the negative pressure and the number of air bubbles in the predetermined time interval is greater than a predetermined limit value for a rate of air bubbles, and/or the second defective condition when the measured negative pressure is below the predetermined limit value for the negative pressure and the number of air bubbles in the predetermined time interval is greater than the predetermined limit value for the rate of air bubbles.

3. The device according to claim 2, wherein the processing unit is programmed to specify the predetermined limit value for the negative pressure as a function of haematocrit.

4. The device according to claim 3, wherein the processing unit is programmed to reduce the predetermined limit value for the negative pressure with an increasing level of the haematocrit.

5. The device according to claim 3, further comprising:
an apparatus adapted to measure the haematocrit, which generates a measurement signal correlated to the haematocrit which is received by the processing unit.

6. The device according to claim 1, wherein the processing unit generates a control signal when the first and/or second defective condition is deduced.

7. The device according to claim 6, further comprising:
an alarm unit, which receives the control signal of the processing unit and gives an acoustic, optical and/or tactile alarm when the alarm unit receives the control signal of the processing unit.

8. A device for extracorporeal blood treatment, comprising:
an extracorporeal blood circuit, and
a device for monitoring the extracorporeal blood circuit according to claim 1.

9. The device according to claim 8, wherein the extracorporeal blood circuit comprises a blood treatment unit and an arterial blood line leading to the blood treatment unit and a venous blood line leading from the blood treatment unit, wherein the blood pump is positioned in the arterial blood line.

10. The device according to claim 8, further comprising:
a control unit adapted to actuate the blood pump with a predetermined blood flow rate, wherein the control unit is adapted to reduce the blood flow rate from a predetermined first rate to a predetermined second rate when the apparatus adapted to detect the occurrence of air bubbles in the extracorporeal blood circuit detects air bubbles and the measured negative pressure is above the predetermined limit value for the negative pressure.

11. A method for monitoring an extracorporeal blood circuit, in which a blood pump is disposed to convey blood, the method comprising:
detecting occurrence of air bubbles in the blood that flows in the extracorporeal blood circuit,
measuring a negative pressure in the extracorporeal blood circuit upstream of the blood pump, and
deducing a first defective condition when the occurrence of bubbles is detected in the extracorporeal blood circuit and the measured negative pressure is above a predetermined limit value for the negative pressure, and/or a second defective condition when the occurrence of air bubbles is detected in the extracorporeal blood circuit and the measured negative pressure is below the predetermined limit value for the negative pressure,
wherein the first defective condition differs from the second defective condition.

12. The method according to claim 11, further comprising:
determining a number of air bubbles occurring in a predetermined time interval, and
deducing the first defective condition when the measured negative pressure is above the predetermined limit value for the negative pressure and the number of air bubbles in the predetermined time interval is greater than a predetermined limit value for a rate of air bubbles, and/or the second defective condition when the measured negative pressure is below the predetermined limit value for the negative pressure and the number of air bubbles in the predetermined time interval is greater than the predetermined limit value for the rate of air bubbles.

13. The method according to claim 12, further comprising:
specifying the predetermined limit value for the negative pressure as a function of haematocrit.

14. The method according to claim 13, wherein the predetermined limit value for the negative pressure is reduced with increasing level of the haematocrit.

15. The method according to claim 13, further comprising:
measuring the haematocrit during the blood treatment.

16. The method according to claim 11, further comprising:
giving an acoustic, optical and/or tactile alarm when the first and/or second defective condition is detected.

17. The method according to claim 11, further comprising:
reducing a blood flow rate at which the blood flows in the extracorporeal blood circuit from a predetermined first rate to a predetermined second rate when the occurrence of air bubbles is detected in the extracorporeal blood circuit and the measured negative pressure is above the predetermined limit value for the negative pressure.

* * * * *